United States Patent [19]
Hueton et al.

[11] Patent Number: 5,459,325
[45] Date of Patent: Oct. 17, 1995

[54] HIGH-SPEED FLUORESCENCE SCANNER

[75] Inventors: Iain Hueton, Los Altos Hills; Ezra Van Gelder, Belmont, both of Calif.

[73] Assignee: Molecular Dynamics, Inc., Sunnyvale, Calif.

[21] Appl. No.: 277,900

[22] Filed: Jul. 19, 1994

[51] Int. Cl.⁶ ................................................. G01N 21/64
[52] U.S. Cl. ...................... 250/458.1; 356/317; 356/318
[58] Field of Search ............................. 250/458.1, 461.1, 250/461.2; 356/317, 318, 417

[56] References Cited

U.S. PATENT DOCUMENTS

| | | | |
|---|---|---|---|
| 4,684,797 | 8/1987 | Ando et al. | 250/201 |
| 4,712,887 | 12/1987 | Baer | 350/484 |
| 4,877,966 | 10/1989 | Tomei et al. | 250/458.1 |
| 4,881,812 | 11/1989 | Ohkubo et al. | 356/417 |
| 5,001,694 | 3/1991 | Lee et al. | 369/44.16 |
| 5,060,213 | 10/1991 | Kamisada | 367/44.21 |
| 5,088,079 | 2/1992 | Baer | 369/44.26 |
| 5,091,652 | 2/1992 | Mathies et al. | 250/458.1 |
| 5,195,074 | 3/1993 | Tanoshima et al. | 369/48 |
| 5,196,709 | 3/1993 | Berndt et al. | 250/458.1 |
| 5,218,461 | 6/1993 | Aoyama et al. | 358/471 |
| 5,274,240 | 12/1993 | Mathies et al. | 250/458.1 |
| 5,293,363 | 3/1994 | Takeshita | 369/44.21 |

*Primary Examiner*—Carolyn E. Fields
*Attorney, Agent, or Firm*—Schneck & McHugh

[57] ABSTRACT

A high-speed fluorescence scanner for scanning a sample at equal angles is disclosed. The scanner has most of its optical components, including a light beam source, a detector, and various filters, lenses, and reflectors, in a fixed position, removed from the scan head. The lightweight scan head contains a single reflector and lens combination which is reciprocated rapidly along one axis to lengthen and shorten a region of the path of a collimated excitation beam and to form a scan line on a sample. The fluorescence emission may be gathered by the lens of the scan head and directed back, generally along the optical path of the excitation beam, to a detector. Another embodiment of the scanner places the light source, in miniature form, directly on the scan head. The sample may be translated in an axis orthogonal to the scan line in order to stimulate fluorescent emission from a two-dimensional portion of the sample. The design of the optical assembly currently permits scan speeds of up to approximately 100 inches per second.

31 Claims, 5 Drawing Sheets

HIGH-SPEED FLUORESCENCE SCANNER

TECHNICAL FIELD

This invention relates to optical scanners for stimulating and reading fluorescence emission from a target.

BACKGROUND ART

Fluorescence scanners generally scan samples via stimulation by a light beam at an excitation wavelength, in a one or two-dimensional manner. The resulting stimulated fluorescent emission, which typically occurs at a different wavelength or wavelength band, is then detected. One type of scanner requires movement of an excitation beam in one axis and movement of a mechanical stage in an orthogonal axis so that successive straight line scans sequentially cover a two-dimensional area of the sample. Alternatively, the stage may be in a fixed position and the laser beam may be scanned along two axes. Also, the sample may be translated on an X-Y stage and viewed with a microscope or similar fixed optical viewer.

The movement of a light beam to effect scanning in most fluorescence scanners is generally accomplished via galvanometer scanners and rotating polygonal mirrors. These devices are best suited for wide angle scanning, as is necessary for detecting fluorescence emission from planar DNA sequencing gels.

It is important in certain applications to cause stimulation of fluorescence emission from a constant angle at all points of the specimen being scanned. There are inherent difficulties in adapting the above scanning systems to such a situation because the scanning beams have some rotational motion and distortions of fluorescence imaging at various locations of the specimen may occur. Aberrations may be minimized through an fΘ lens which, in conjunction with one of the above scanning mechanisms, provides correction of scan angle and speed and allows for scanning of a flat specimen with an incident beam. Such lenses are quite expensive, however. The costs of some of these scanning mechanisms is also very high.

A wide variety of scan formats is necessary for many research and diagnostic applications. In particular, smaller experimental formats are emerging, such as the scanning of nucleic acid samples on small chips and electrophoresis within capillary tubes. Miniaturization of the effective scanning areas of existing fluorescent scanners requires intricate and expensive adaptation of optical assemblies and is, therefore, not feasible.

It is also desirable to increase scan speed without compromising resolution in order to scan many samples in a short period of time. Existing scanners are limited with respect to scan speed and resolution because of their numerous components and the high mass of their optical assemblies, and also because they are optimized to particular scan angles and sample sizes.

It is therefore an object of the present invention to provide a versatile fluorescent scanner of simple, lightweight, low-cost design for rapid scanning of a small format sample from a constant angle.

DISCLOSURE OF THE INVENTION

The above object has been achieved with a high-speed fluorescence scanner having rapid linear movement of a lightweight scan head containing only a single reflector and lens combination. The excitation beam is collimated and directed to the scan head from a constant angle, and movement of the scan head maintains a uniform angle of illumination on a sample or target. The effect of moving the scan head is continual lengthening and shortening of a region of the excitation beam's path to create a scan line in an image plane. Fluorescence emission from a sample placed within the image plane along the scan line of the excitation beam may be gathered by the lens of the scan head and directed back, generally along the optical path of the excitation beam, to a detector. The low mass of the scan head allows for high speed scanning. The scan head is driven by a linear actuator operable at up to approximately 100 inches per second. A sample may be moved orthogonally past the scan line for two-dimensional scanning, as by translation of a stage or by electrophoresis. The fluorescence scanner of the present invention may be adapted through substitution of lenses and reflectors of various sizes and corresponding mechanical adjustments to provide for scanning and fluorescent imaging of samples in a wide variety of sizes and formats.

Another embodiment of the present invention places the light source, in a miniature form, directly on the scan head. The scan head contains the light source and the lens. It may also contain a dichroic beam splitter or other means for separating the excitation beam from the fluorescence emission and for directing the fluorescence emission away from the scan head and toward a detector. In this alternate embodiment, there may be a fixed reflector, removed from the scan head, that is positioned to receive the fluorescence emission and deflect it toward the detector. Reciprocating motion of the scan head by the linear actuator in this instance causes a continual lengthening and shortening of the region of the fluorescence emission's path between the scan head and the reflector.

The use of the term "reflector" includes mirrors and penta prisms. The use of the term "lens" signifies a single or multi-element lens.

An advantage of the present invention over previous fluorescence scanners is the rapid stimulation of samples at a constant angle without resort to expensive corrective optics. In other words, the relative position of the scan head and the sample is maintained.

Another advantage is the simple, lightweight design of the scan head and of the optical paths taken by the excitation beam and the fluorescence emission, which allow for a rapid scanning motion and for ease of adaptability to many applications.

BEST MODE OF CARRYING OUT THE INVENTION

Figure 1:
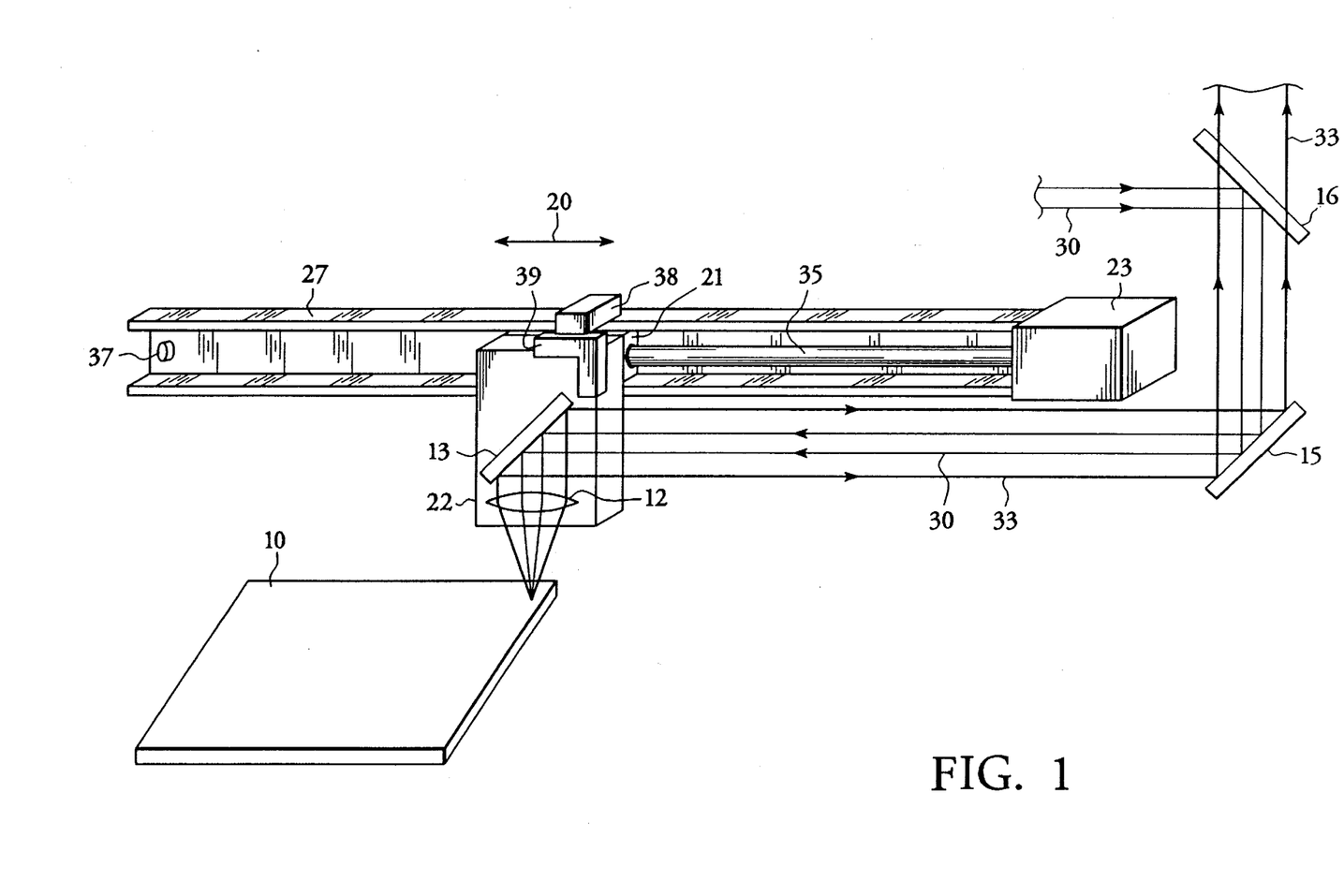
FIG. 1 shows a scan head with accompanying support, and a portion of the optical assembly according to the present invention.

With reference to FIG. 1, a low-mass scan head 22 is shown to contain a reflector 13 and a lens 12. The use of the term "reflector" includes mirrors and penta prisms. The use of the term "lens" signifies a single or multi-element lens.

Both reflector 13 and lens 12 are fixed in a given planar orientation within scan head 22, according to the desired optical scan angles. Lens 12 may be adjusted within the given planar orientation to achieve centration. Scan head 22 may be attached to a bearing 21 which is slidably attached to a guide 27. In FIG. 1, guide 27 is shown as a U-shaped channel within which scan head 22 moves in direction 20. Linear actuator 23 is positioned at one end of guide 27 in the preferred embodiment and is in communication with scan head 22 through shaft 35, causing scan head 22 to reciprocate in direction 20 along guide 27, which shifts the overall position of reflector 13 and lens 12 and performs a scan in one dimension on image plane 10. Stop 37 is positioned at an end of guide 27 opposite linear actuator 23 and functions simply to keep bearing 21 on guide 27. Guide 27 may be mechanically supported at one or both opposing ends. The illustrated mechanical assembly shown is one example of a means of reciprocating scan head 22 linearly. Other means for rapid linear reciprocation may be substituted, such as an elongated arm having a movable member on which scan head 22 is mounted.

Figure 2:
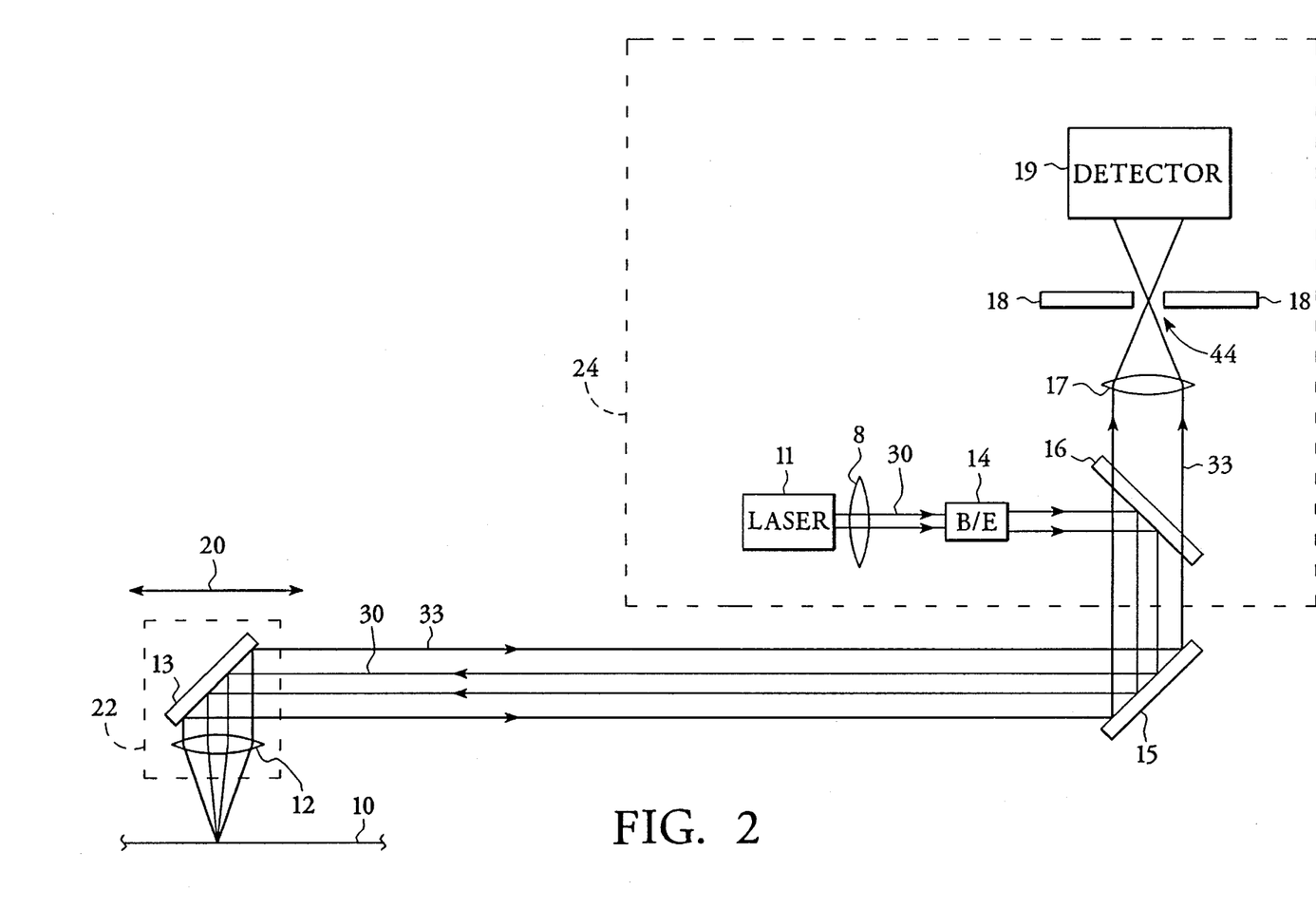
FIG. 2 shows a plan view of the fluorescence scanner of the present invention, with optical assembly details.

With reference to FIG. 2, a complete diagram of one embodiment of the optical pathways is shown. The fluorescence scanner of the present invention generally has a fixed region 24 and a movable region defined by scan head 22. According to the preferred embodiment, within fixed region 24, laser 11 emits a beam 30 at an excitation wavelength. Excitation beam 30 is collimated and optionally expanded by a pass through beam expander 14. A collimated white light source may also be used for excitation. A spectral dispersion device 16, such as a dichroic beam splitter, is placed within the path of excitation beam 30. Excitation beam 30 passes from spectral dispersion device 16 and then impinges upon a reflector 15 which is oriented at an approximately 45° angle to the incident excitation beam 30 in the preferred embodiment. Excitation beam 30 is then deflected in an orthogonal direction and moves away from fixed region 24 of FIG. 2 and enters scan head 22 by impinging upon reflector 13. The reflector 13 is also preferably placed at an approximately 45° angle to the incident excitation beam 30. Excitation beam 30 is then deflected in an orthogonal direction by reflector 13. Lens 12, which generally has a clear aperture between one and twenty times greater than excitation beam 30, is positioned with its axis orthogonal to an image plane 10 so that it receives and focuses excitation beam 30 on image plane 10. Excitation beam 30 effects stimulation of fluorescent emission from samples or targets which are placed within image plane 10.

Movement of scan head 22 in direction 20, as illustrated in FIGS. 1 and 2, causes a continual lengthening and shortening of the region of the collimated beam's path between reflectors 15 and 13 and results in scanning along one axis in image plane 10 while minimizing changes to the optical characteristics of beam 30 at image plane 10. The resulting fluorescence scanning resembles scanning by an optical disk read-head in preservation of beam properties. Motion of scan head 22 may be over long paths, such as several meters in length, or may be over short paths, such as less than one centimeter.

Figure 3A:
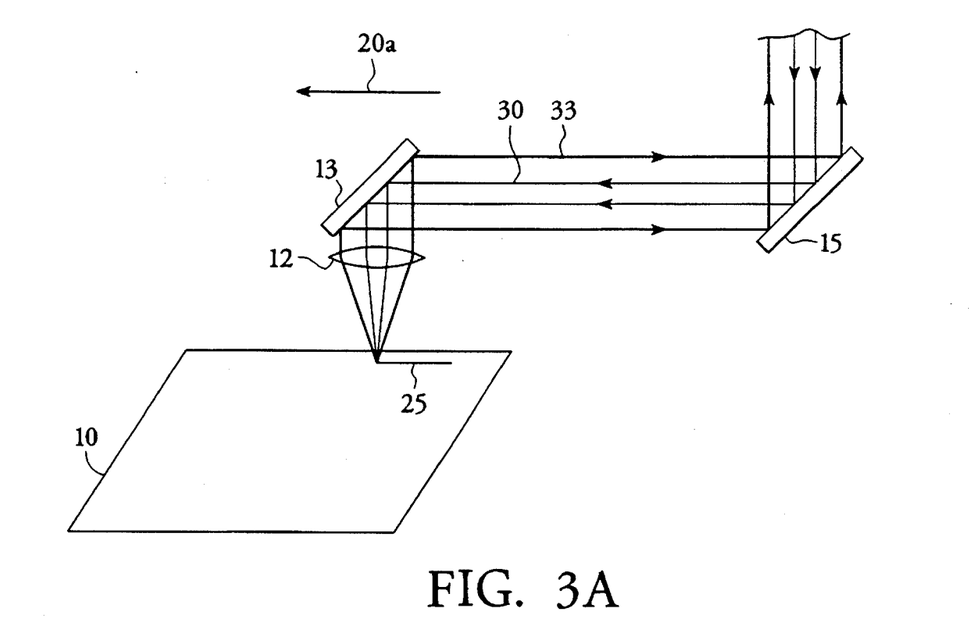
FIGS. 3A-B show a perspective view of a portion of the fluorescence scanner of the present invention, illustrating scan lines and two-dimensional fluorescence stimulation.
Figure 3B:
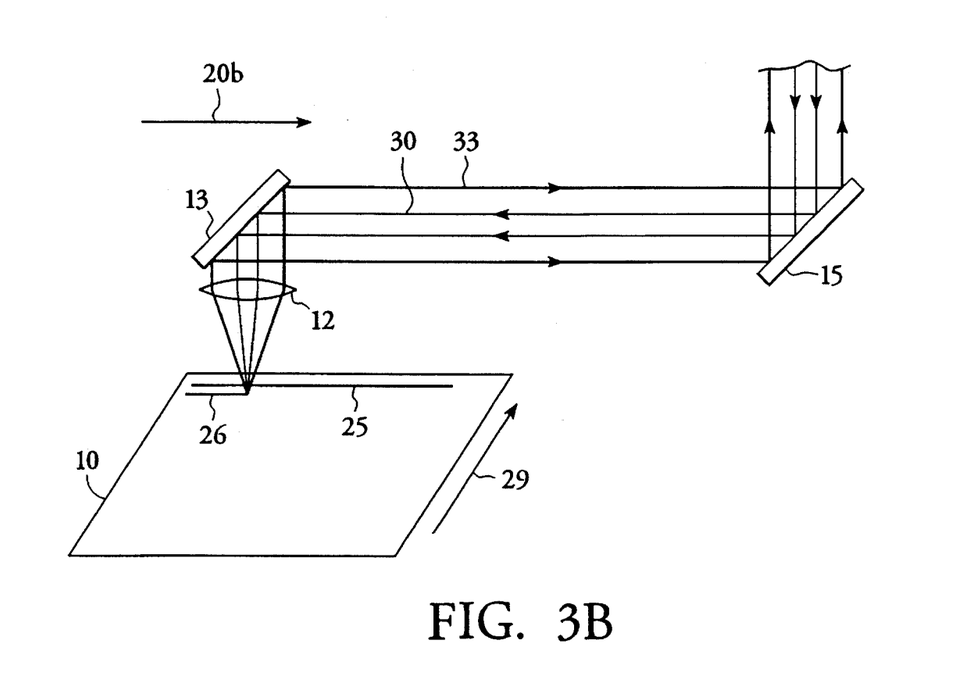

FIGS. 3A–B more clearly illustrate the creation of scan lines. As the path of excitation beam 30 is lengthened between reflectors 15 and 13 by movement of scan head 22, in conjunction with linear actuator 23, in direction 20a, the combination of reflector 13 and lens 12 moves in direction 20a to form scan line 25, as shown in FIG. 3A. In the same manner, as the path of excitation beam 30 is shortened by movement of scan head 22 in direction 20b, scan line 26 is formed. Scan line 26 may be superimposed on scan line 25. If there is a shift of the sample within image plane 10 in a direction orthogonal to scan line 25, however, as indicated by arrow 29, then scan line 26 will be parallel to scan line 25, as illustrated in FIG. 3B. Continual small shifts of the sample in direction 29 will cause formation of successive scan lines and result in two-dimensional fluorescent stimulation of the sample in image plane 10.

Figure 4:
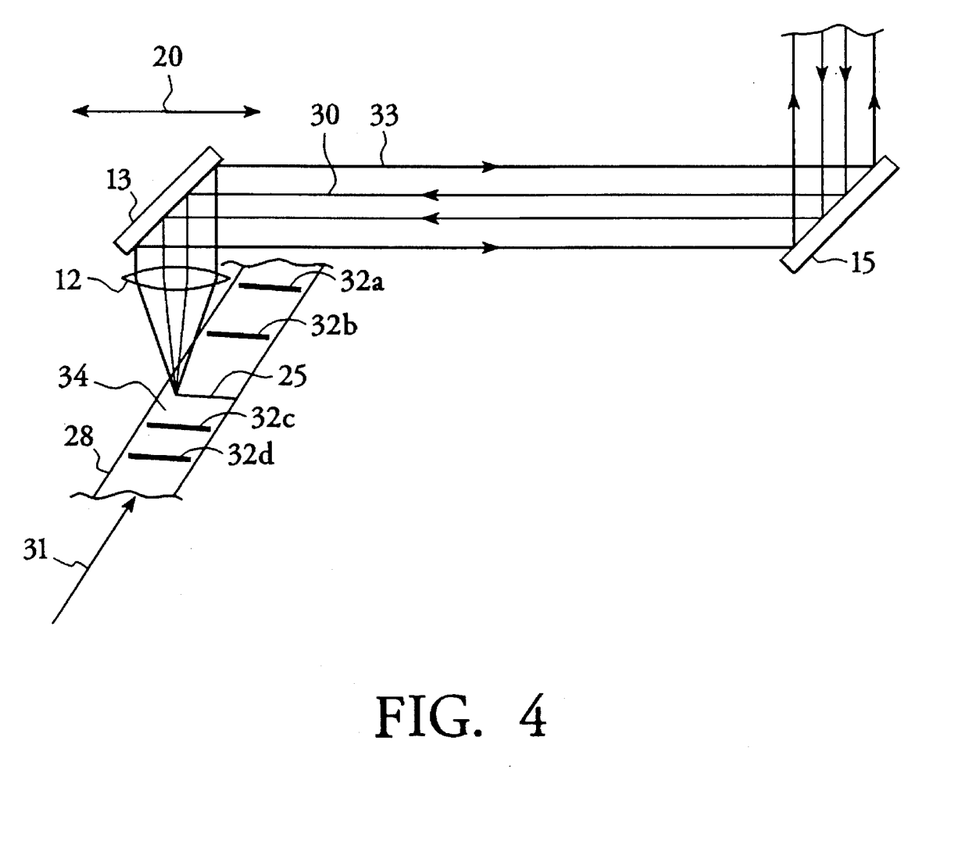
FIG. 4 shows a perspective view of a portion of the fluorescence scanner of the present invention, illustrating translation in one dimension by electrophoresis.

The movement of the sample in direction 29 may be accomplished by providing a stage for placement of the sample within image plane 10 and then by translation of the stage, as by a lead screw connected to a motor or another type of linear actuator. Alternatively, the sample may be translated in image plane 10 across the scan line by electrophoretic or other means. FIG. 4 gives an example of movement of a sample in one dimension by electrophoresis. Various components 32a–d of the sample are driven in direction 31 through a matrix 34 within lane 28 by application of an electric field. Scan line 25 represents a scan in the direction 20 orthogonal to the direction 31 of sample movement. Continued electrophoretic movement of the sample components across the scan line allows for fluorescence detection of the entire sample over a period of time. For simplicity, FIG. 4 has been illustrated with only a few widely-spaced sample bands. The present invention is equally applicable, however, to fluorescent scanning of multiple closely-spaced sample bands and to multiple lanes of samples.

Returning to FIG. 2, fluorescent emission by a sample placed within image plane 10 and scanned according to the present invention is gathered, in the preferred embodiment, by lens 12, which has a high numerical aperture and gathers fluorescence over a large angle. The term "high numerical aperture" means that the lens has a wide diameter for collected light, which is only fractionally used by the incoming beam, compared to its focal length. The gathered fluorescence is directed along a path substantially retracing the path of excitation beam 30. Fluorescence emission 33 passes to reflector 13 and then to reflector 15. It is then directed to spectral dispersion device 16, which is positioned in the path of both the excitation beam 30 and the fluorescence emission 33, and operates to separate excitation from fluorescence emission via their unique spectral characteristics. After the fluorescence emission 33 is separated by spectral dispersion device 16, it is passed through a lens 17 and is then focused within an aperture 44 of a spatial filter 18 and detected by a photosensitive detector 19, such as a photomultiplier tube or a photocell. The use of spatial filter 18 is optional and is dependent upon the types of samples being scanned and the particular parameters of fluorescence detection necessary for such samples.

Figure 5:
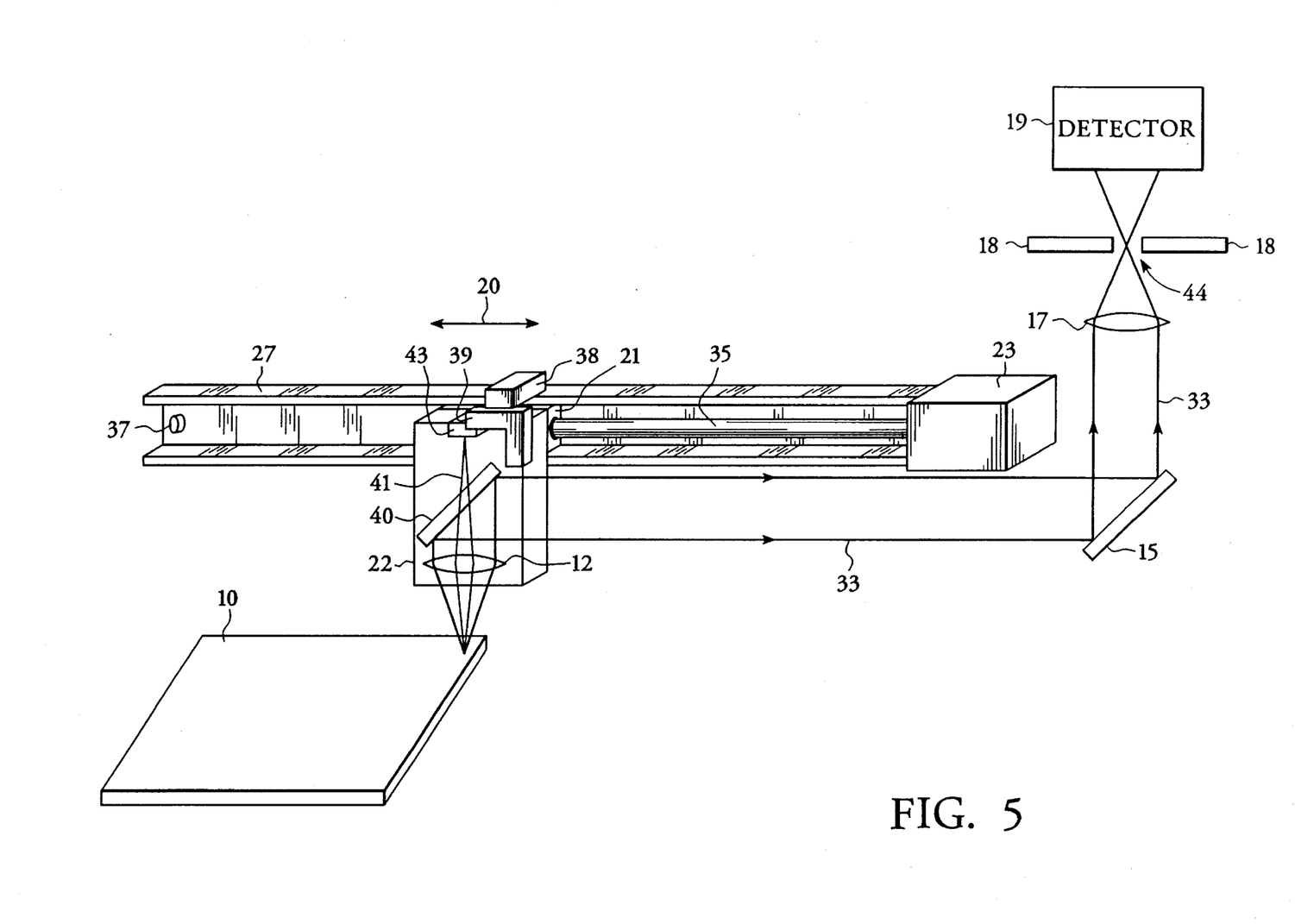
FIG. 5 shows an alternate embodiment of the present invention, with details of the scan head and optical assembly.

By way of illustration, light sources for the present invention may include semiconductor or gas lasers, laser diodes, and may even be pulsed. A light emitting diode may also be used. FIG. 5 shows an alternate embodiment of the present invention, utilizing a miniature light source such as a laser diode, LED, halogen lamp, or xenon lamp. If the light source is in a miniature form, and therefore of low mass, it may be mounted directly on the scan head, instead of being in a fixed position removed from the scan head. Laser diode 43 is shown in FIG. 5 as one example of a light source appropriate for the second embodiment. The excitation beam 41 emitted by laser diode 43 does not need to be collimated in this instance. Excitation beam 41 passes through a spectral dispersion device 40, such as a dichroic beam splitter, and then passes through lens 12. Lens 12 focuses excitation beam 41 on the image plane to stimulate fluorescence emission. The resulting emission is generally gathered through the wide collection angle of lens 12 and then collimated. Fluorescence emission 33 then is directed out of scan head 22, preferably by spectral dispersion device 40, which separates fluorescence emission 33 from excitation beam 41. Reflector 15 is placed in the path of fluorescence emission 33, preferably at an approximately 45° angle, and serves to deflect fluorescence emission 33 to lens 17 for detection as in the first embodiment of the present invention. Reciprocation of scan head 22 by linear actuator 23 causes scanning in one axis and the sample may be translated in another axis, as in the first embodiment. Fluorescence emission 33 is thus transmitted along the axis of travel of the scan head.

Within the optical assembly, the beam spot size and shape may be varied through the use of particular beam expanders and lenses. The depth of focus of the excitation beam is dependent upon the beam spot size and the focusing characteristics of lens 12. Scanning may occur in a confocal or nonconfocal format in the present invention. In addition, fluorescence detection may occur in a manner that does not require retracing of the fluorescence emission along substantially the same optical path as that taken by the excitation beam.

Although beam paths parallel and orthogonal to the image plane have been illustrated for simplicity, positions of the optical components and the image plane may be altered depending on the application. For example, the direction from which excitation beam 30 impinges upon reflector 13 and the orientations of reflector 13 and lens 12 within scan head 22 may be altered. Image plane 10 may also be shifted so that it is no longer parallel to the direction of linear motion of scan head 22 or so it receives excitation beam 30 at all scan points from other than an orthogonal direction. As long as reflector 13 receives excitation beam 30 at a constant angle and the scan head components have been oriented to impinge upon a sample placed in an image plane, then linear reciprocation of the scan head in certain directions will cause scanning of the sample.

The overall positions of the components of the fluorescence scanner of the present invention may also be shifted. For example, a sample may be mounted in a vertical image plane, the fixed region 24 may be positioned along a horizontal optical base plate, and the reciprocation mechanism illustrated in FIG. 1 may be mounted on the base plate via a rigid bracket, so that linear actuator 23 causes scan head 22 to move vertically. This is the preferred positioning for scanning of samples such as vertical electrophoresis gels.

According to the present invention, scan head 22 may reciprocate in a continual fashion and the laser scanner may operate for simple detection of fluorescent emission. For example, scan head 22 accelerates and reaches an optimum scan velocity at a known position along guide 27. In FIG. 1, sensor 38, which is positioned on guide 27, and flag 39, which is attached to scan head 22, operate in conjunction to mark the known home position of optimum scan velocity. Stimulation and reading of fluorescence then occurs for a period of time along the length of a scan line, after which the scan head decelerates and a new sample or line to be scanned may be placed within the scan line of excitation beam 30 within image plane 10, e.g. via shifting of the sample in direction 29 of FIG. 3B. Successive, closely-spaced scans sequentially cover two dimensions in image plane 10. Alternatively, the laser scanner may be in communication with an image processing means whereby the scan mechanism collects fluorescence information from the sample in a location-specific manner, as by determination of fluorescence intensity within pixels approximating the beam spot size. This information may then be manipulated, e.g., to form a display of fluorescence locations. Reciprocation of scan head 22 in a continual, oscillating, or step-wise manner is anticipated.

The scan head 22 and linear actuator 23 of the present invention generally operate in an open loop mode for data acquisition for image processing. For example, a command module may be attached to linear actuator 23 which sends scan head 22 out in one direction, as in direction 20a of FIG. 3A, to a specified spot location, i.e. an address, then stops scan head 22 and sends it back in direction 20b of FIG. 3B. A closed loop mode may also be used depending on the accuracy required. The linear actuator may be of the type used in optical disk read-heads, except that the head may be supported at opposed ends, rather than being cantilevered or otherwise supported from just one end. The seek time to a single spot is preferably under 500 milliseconds, and more preferably under 50 milliseconds.

The simple lightweight design and high scan speed of the present invention represent a significant advancement over the prior art. The scan head 22 is the only portion of the optical assembly that moves while scanning. The light beam source, detector, and various filters, lenses, and reflectors are in a fixed position, removed from scan head 22. The weight of scan head 22 is preferably under five hundred grams. The use of a miniature lens 12 and miniature reflector 13 further contributes to the light weight, and consequently, to the rapid scan speed. Linear actuator 23 is designed to operate in the range of 3 to 25 Hz and provide a scan speed of approximately 100 inches per second with current linear actuators. Examples of linear actuators appropriate to the present invention include voice coils, cams, belts, cranks, or lead screws connected to a motor to reciprocate scan head 22, preferably in the axis represented by arrow 20. These linear actuators are preferably similar, in speed, accuracy and preservation of beam properties, to those used in optical disk read-heads.

The on-axis configuration of the present invention also has the advantage of ensuring that excitation light impinges upon the sample at the same angle for all points of the sample in image plane 10. This is not the case with galvanometer scanners, polygonal mirrors, or raster systems. The present configuration allows for the use of less expensive lenses and eliminates aberrations associated with pin cushion distortions, field curvature, and diffraction limiting lenses.

The apparatus of the present invention may be used to detect the fluorescence of samples within gels, slides, dishes, capillary tubes, microtiter plates, cuvettes, or other formats in which high resolution, rapid scanning is necessary. Although a high-speed microscanner has been more particularly described, the present invention may be configured to operate on larger samples. With the optical configuration of the present invention and minor adaptations to sizes and speeds of the various components, fluorescence scanning of samples in a wide variety of formats is possible.

Simple adaptation to the present invention may also be made to allow for fluorescence detection in the Z-direction, or depthwise through the sample. This may be accomplished, e.g., through shifting of the sample stage to planes parallel to image plane 10 or by adding a movement of or within scan head 22 to cause a raising or lowering of the beam spot through the sample.

Optical fibers to transmit the excitation beam or fluorescence emission along various portions of the optical path in the present invention may also be used.

We claim:

1. A high-speed optical scanner for directing a beam at equal angles at a plurality of locations on a sample in an image plane comprising, means for producing a collimated excitation beam of light having a first spectral characteristic, a scan head having
   (i) a reflector disposed to receive the excitation beam at a constant angle and to deflect the excitation beam, and
   (ii) a lens disposed to intercept the excitation beam deflected by the reflector and to focus the excitation beam to a location on the sample in the image plane to cause fluorescent emission having a second spectral characteristic from the sample, and to gather the fluorescent emission from the sample, the fluorescent emission being directed back to the reflector, actuator means for reciprocally moving the scan head in a linear direction, whereby the excitation beam impinges upon the sample within the image plane in a scan line, a spectral dispersion device for separating the spectral characteristics of fluorescent emission from the spectral characteristics of excitation.

2. The scanner of claim 1 wherein the reflector receives the excitation beam from a direction parallel to the direction of motion of the means for reciprocally moving the scan head.

3. The scanner of claim 2 wherein the reflector is oriented at an approximately 45° angle to the image plane, and the lens is positioned with its axis orthogonal to the image plane, whereby the excitation beam impinges upon the sample within the image plane from an orthogonal direction at all points in the scan line.

4. The scanner of claim 1 wherein the actuator means is characterized by a scan speed of up to approximately 100 inches per second.

5. The scanner of claim 1 wherein the actuator means comprises a shaft mechanically coupled to the scan head, the shaft being driven axially by a motor.

6. The scanner of claim 1 further comprising a means for translating the sample in the image plane in a direction orthogonal to the direction of the scan line, so that successive scans of the excitation beam sequentially cover two dimensions in the image plane.

7. The scanner of claim 1 further comprising an electrophoretic means for moving the sample in a direction orthogonal to the scan line.

8. The scanner of claim 1 wherein the means for reciprocally moving the scan head comprises a linear actuator operating on an open loop mechanism.

9. The scanner of claim i wherein the means for reciprocally moving the scan head comprises a linear actuator operating on a closed loop mechanism.

10. The scanner of claim 1 wherein the means for producing a collimated excitation beam comprises, a laser emitting an excitation beam, and a collimating lens positioned in the path of the excitation beam.

11. The scanner of claim 1 further comprising, a second lens positioned proximate to the spectral dispersion device, for focusing the fluorescent emission, which has been separated from the excitation beam by the spectral dispersion device, and a light detector responsive to fluorescent emission.

12. The scanner of claim 11 further comprising, a spatial filter positioned between the second lens and the light detector and having a pinhole aperture, the pinhole aperture disposed to intercept the fluorescence emission and to admit a portion thereof.

13. A high-speed optical scanner for directing a beam at equal angles at a plurality of locations on a sample in an image plane comprising, a scan head having
    (i) means for producing an excitation beam of light having a first spectral characteristic,
    (ii) a lens disposed to intercept the excitation beam and to focus the excitation beam to a location on the sample in the image plane to cause fluorescent emission having a second spectral characteristic from the sample, and to gather the fluorescent emission from the sample,
    (iii) means for directing the fluorescent emission out of the scan head, and
    (iv) a spectral dispersion device for separating the spectral characteristics of fluorescent emission from the spectral characteristics of excitation, and actuator means for reciprocally moving the scan head in a linear direction, whereby the excitation beam impinges upon the sample within the image plane in a scan line.

14. The scanner of claim 13 wherein the means for directing the fluorescent emission out of the scan head and the spectral dispersion device are a single dichroic beam splitter, the dichroic beam splitter positioned between the lens and the means for producing an excitation beam.

15. The scanner of claim 13 wherein the means for producing an excitation beam is a light source selected from the group consisting of a laser diode, an LED, a halogen lamp, and a xenon lamp.

16. The scanner of claim 13 wherein the actuator means is characterized by a scan speed of up to approximately 100 inches per second.

17. The scanner of claim 13 wherein the actuator means comprises a shaft mechanically coupled to the scan head, the shaft being driven axially by a motor.

18. The scanner of claim 13 further comprising a means for translating the sample in the image plane in a direction orthogonal to the direction of the scan line, so that successive scans of the excitation beam sequentially cover two dimensions in the image plane.

19. The scanner of claim 13 further comprising an electrophoretic means for moving the sample in a direction orthogonal to the scan line.

20. The scanner of claim 13 wherein the means for reciprocally moving the scan head comprises a linear actuator operating on an open loop mechanism.

21. The scanner of claim 13 wherein the means for reciprocally moving the scan head comprises a linear actuator operating on a closed loop mechanism.

22. The scanner of claim 13 further comprising, a light detector responsive to the fluorescent emission, the light detector being positioned in the path of the fluorescent emission away from the scan head, and a second lens positioned in the path of the fluorescent emission between the scan head and the light detector, for focusing the fluorescent emission toward the light detector.

23. The scanner of claim 22 further comprising, a spatial filter positioned between the second lens and the light detector and having a pinhole aperture, the pinhole aperture disposed to intercept the fluorescence emission and to admit a portion thereof.

24. A high-speed optical scanner for directing a beam at equal angles at a plurality of locations over extended targets comprising, an elongated arm, supported in an X-line, supporting a movable member adapted to be driven, linear actuator means for driving the member, means for producing a collimated beam of light parallel to the arm, a stage supporting a target to be scanned, the target containing material which fluoresces in response to impingement by the beam, an optical assembly, having a light reflector and an objective lens, the optical assembly mounted to the movable member of the arm, the reflector disposed to intercept the beam and direct the beam into the objective lens, the objective lens having a clear aperture between one and twenty times greater than the beam diameter and a focal spot on the target whereby the diameter of the objective lens functions as a light collector for fluorescent light, directing the light in a retropath parallel to the beam, a dichroic optical element disposed in the beam path, separating collected fluorescent light from the beam.

25. The scanner of claim 24 further comprising means for translating the target in a Y-line.

26. An optical scanner for rapid stimulation and fluorescence detection of samples comprising, an optical assembly having
  (i) a light source emitting an excitation beam,
  (ii) a collimator positioned proximate to the light source,
  (iii) a first reflector positioned at an angle in the path of the excitation beam, whereby the excitation beam is received by the first reflector and deflected,
  (iv) a second reflector positioned at an angle in the path taken by the excitation beam after it has been deflected by the first reflector, whereby the excitation beam is received by the second reflector and deflected,
  (v) a first lens positioned proximate to the second reflector in the path taken by the excitation beam after it has been deflected by the second reflector, whereby the excitation beam is received by the first lens and focused onto a sample to stimulate fluorescence emission therefrom, and whereby the fluorescence emission is gathered by the first lens and directed generally along the path taken by the excitation beam,
  (vi) a spectral dispersion device positioned in the path of the excitation beam and the gathered fluorescence emission, whereby the fluorescence emission is separated from the excitation beam by spectral characteristics, and
  (vii) a detector responsive to fluorescence emission positioned in the path taken by the fluorescence emission after it has been deflected by the second reflector, a movable support carrying the second reflector and the first lens, and an actuator for reciprocating the movable support in a linear direction, whereby the path of the excitation beam between the first and second reflectors is lengthened and shortened and the excitation beam impinges upon the sample in a scan line.

27. The optical scanner of claim 26 further comprising a second lens positioned proximate to the spectral dispersion device in the path taken by the fluorescence emission after it has been separated by the spectral dispersion device, and a spatial filter having a pinhole aperture, the spatial filter positioned between the second lens and the detector, the pinhole aperture disposed to intercept and admit only a portion of the fluorescence emission.

28. The optical scanner of claim 26 further comprising a fixed guide attached to the movable support, the movable support reciprocating along the fixed guide.

29. An optical scanner for rapid stimulation and fluorescence detection of samples comprising, an optical assembly having
  (i) a light source emitting an excitation beam,
  (ii) a first lens positioned proximate to the light source whereby the excitation beam is received by the first lens and focused onto a sample to stimulate fluorescence emission therefrom, and whereby the fluorescence emission is gathered by the first lens,
  (iii) a spectral dispersion device positioned in the path of the excitation beam and the gathered fluorescence emission, whereby the fluorescence emission is separated from the excitation beam by spectral characteristics,
  (iv) a reflector positioned to receive the fluorescence emission after it has been separated by the spectral dispersion device and to deflect the fluorescence emission, and
  (v) a detector responsive to fluorescence emission positioned in the path taken by the fluorescence emission after it has been deflected by the reflector, a movable support carrying the light source, the spectral dispersion device, and the first lens, and an actuator for reciprocating the movable support in a linear direction, whereby the excitation beam impinges upon the sample in a scan line.

30. The optical scanner of claim 29 further comprising, a second lens positioned to receive and to focus the fluorescence emission after it has been deflected by the reflector, and a spatial filter having a pinhole aperture, the spatial filter positioned between the second lens and the detector, the pinhole aperture disposed to intercept and admit only a portion of the fluorescence emission.

31. The optical scanner of claim 29 further comprising a fixed guide attached to the movable support, the movable support reciprocating along the fixed guide.

* * * * *